United States Patent [19]

Miyazawa et al.

[11] Patent Number: 5,105,018
[45] Date of Patent: Apr. 14, 1992

[54] PROCESS FOR HYDROFORMYLATION OF AN OLEFIN

[75] Inventors: Chihiro Miyazawa; Hiroshi Mikami, both of Kurashiki, Japan

[73] Assignee: Mitsubishi Kasei Corporation, Tokyo, Japan

[21] Appl. No.: 596,383

[22] Filed: Oct. 12, 1990

[30] Foreign Application Priority Data

Oct. 19, 1989 [JP] Japan .................................. 1-272275

[51] Int. Cl.$^5$ .......................................... C07C 45/50
[52] U.S. Cl. .................... 568/453; 568/451; 588/454
[58] Field of Search ................ 568/454, 451, 449, 453

[56] References Cited

U.S. PATENT DOCUMENTS

| | | | |
|---|---|---|---|
| 3,239,566 | 3/1966 | Slaugh et al. | 568/456 |
| 3,518,319 | 6/1970 | Ellert et al. | 568/453 |
| 3,590,087 | 6/1971 | Winkle | 568/854 |
| 3,636,159 | 1/1972 | Solomon | 568/453 |
| 3,868,422 | 2/1975 | Hart et al. | 568/453 |
| 4,528,404 | 7/1985 | Oswald et al. | 561/454 |
| 4,593,127 | 6/1986 | Bunning et al. | 568/454 |

FOREIGN PATENT DOCUMENTS

| | | | |
|---|---|---|---|
| 0157755 | 10/1925 | European Pat. Off. | 568/454 |
| 0016285 | 10/1980 | European Pat. Off. | 568/454 |
| 2053177 | 4/1971 | France | 568/454 |
| 0827476 | 5/1981 | U.S.S.R. | 568/453 |
| 1387657 | 3/1975 | United Kingdom | 568/454 |

Primary Examiner—Werren B. Lone
Attorney, Agent, or Firm—Oblon, Spivak, McClelland, Maier & Neustadt

[57] ABSTRACT

A process for hydroformylation of an olefin, which comprises reacting an olefin with carbon monoxide and hydrogen in the presence of a rhodium catalyst having a trivalent organic phosphorus compound as a ligand, wherein the hydroformylation reaction is conducted by two stage reactor systems i.e., a first stage reactor system comprising a reactor or reactors having a mixing characteristic of the liquid phase being substantially of complete mixing type, and a second stage reactor system being a reaction system of a catalyst solution circulating type and comprising a reactor or reactors having a mixing characteristic of piston flow type wherein when the mixing characteristic of the liquid phase is represented by a diffusion model, a non-dimensional number U (hereafter referred to as a "flow mixing parameter") defined by the formula (I):

$$U = \bar{u}L/2\bar{E} \qquad (I)$$

wherein $\bar{u}$ is an average flow velocity (cm/sec), L is the length (cm) of the reaction layer, and $\bar{E}$ is an average diffusion coefficient (cm$^2$/sec), is at least 0.4, a gaseous product or gas-liquid mixture discharged from the first stage reactor system, is separated into a stream containing the unreacted olefin and other stream, and a part or whole of the stream containing the unreacted olefin is supplied to the second stage reactor system.

22 Claims, 6 Drawing Sheets

PROCESS FOR HYDROFORMYLATION OF AN OLEFIN

The present invention relates to a process for hydroformylation of an olefin, which comprises reacting an olefin with carbon monoxide and hydrogen in the presence of a rhodium catalyst having a trivalent organic phosphorus compound. More particularly, the present invention relates to a process for hydroformylation of an improved reaction system.

It is known to conduct a hydroformylation reaction of an olefin in the presence of a rhodium catalyst. Also with respect to the reaction systems for the hydroformylation reaction, several methods have so far been disclosed.

For example, Japanese Unexamined Patent Publication No. 88816/1974 discloses a method wherein a gas-liquid mixed phase is passed through in a specified direction in 2 or 3 reactors. Japanese Unexamined Patent Publication No. 125103/1977 discloses a reaction system of gas stripping type by means of a single stage complete mixing tank. Further, Japanese Unexamined Patent Publication No. 218546/1986 discloses a reaction system wherein complete mixing tanks are combined for two stage reaction. Furthermore, Japanese Unexamined Patent Publication No. 13295/1980, discloses a reaction system of loop type.

The reaction system for the hydroformylation reaction is required to minimize low boiling point components (hereinafter referred to simply as LB) such as paraffins as reaction byproducts and high boiling point components (hereinafter referred to as HB) as polycondensation products of the formed aldehyde, and at the same time to increase the conversion of the olefin i.e. to reduce the proportion of the unreacted olefin.

The present inventors have conducted extensive studies on the above problems and as a result, have found it possible to solve the problems by conducting the hydroformylation reaction by means of a specific combination of two reactor systems having different mixing characteristics. The present invention has been accomplished on the basis of this discovery.

The present invention provides a process for hydroformylation of an olefin, which comprises reacting an olefin with carbon monoxide and hydrogen in the presence of a rhodium catalyst having a trivalent organic phosphorus compound as a ligand, wherein the hydroformylation reaction is conducted by two stage reactor systems i.e. a first stage reactor system comprising a reactor or reactors having a mixing characteristic of the liquid phase being substantially of complete mixing type, and a second stage reactor system being a reaction system of catalyst solution-circulating type and comprising a reactor or reactors having a mixing characteristic of piston flow type wherein when the mixing characteristic of the liquid phase is represented by a diffusion model, a non-dimensional number U (hereinafter referred to as a "flow mixing parameter") defined by the formula (I):

$$U = \bar{u}L/2\bar{E} \qquad (I)$$

wherein $\bar{u}$ is an average flow velocity (cm/sec), L is the length (cm) of the reaction layer, and $\bar{E}$ is an average diffusion coefficient (cm$^2$/sec), is at least 0.4, a gaseous product or gas-liquid mixture discharged from the first stage reactor system, is separated into a stream containing the unreacted olefin and other stream, and a part or whole of the stream containing the unreacted olefin is supplied to the second stage reactor system.

Now, the present invention will be described in detail with reference to the preferred embodiments.

There is no particular critical limitation to the olefin to be used in the present invention. The olefin may be a single olefin or a mixture of olefins. Preferred is an olefin having from 2 to 5 carbon atoms or a mixture of such olefins. The most preferred olefin is propylene. Further, even a raw material having a low purity of an olefin containing hydrocarbons other than olefins such as paraffins, may also be useful. The olefin material is usually employed without any special pretreatment. However, it is possible to employ the one having a sulfur content or a halogen content, or dienes or trienes, or peroxides, which are known as catalyst poisons, removed by a conventional method such as adsorption, extraction, distillation, thermal treatment, or membrane separation.

As the catalyst, a rhodium catalyst having a trivalent organic phosphorus compound as a ligand, is used. As the trivalent organic phosphorus compound, it is possible to employ not only an organic phosphorus compound having an ability as a trivalent monodentate ligand, such as a trialkyl phosphine such as tributyl phosphine or trioctyl phosphine, a triaryl phosphine such as triphenyl phosphine, tritolyl phosphine or a triaryl phosphine having hydrogen of the phenyl group substituted by a sulfonic group or by halogen, a tricycloalkyl phosphine such as tricyclohexyl phosphine, an alkylaryl phosphine such as monobutyldiphenyl phosphine or dipropylphenyl phosphine, a cycloalkylaryl phosphine, an alkylcycloalkyl phosphine, or a phosphite such as triphenyl phosphite, but also an organic phosphorus compound having ability as a multidentate ligand, represented by the formula:

(wherein each of $R_1$ to $R_4$ is an alkyl group or an aryl group, and Y is a divalent linking group, for example, a hydrocarbon group such as an alkylene group, an oxygen-containing hydrocarbon group such as an alkyleneoxyalkylene group, a sulfur-containing hydrocarbon group such as an alkylenethioalkylene group, or a nitrogen-containing hydrocarbon group such as an alkyleneaminoalkylene group). Further, it is also possible to employ two or more of such compounds as a mixed ligand. It is also possible to employ a trivalent organic phosphorus compound in combination with a pentavalent organic phosphorus compound such as triphenyl phosphine oxide.

As the rhodium source, it is possible to employ not only a rhodium complex such as hydridocarbonyltris(triphenyl phosphine) rhodium or acetoxybis(triphenyl phosphine) rhodium, but also an organic salt such as rhodium acetylacetonate or rhodium acetate, an inorganic salt such as rhodium nitrate, or an oxide such as rhodium oxide. Rhodium may directly be fed into the hydroformylation reactor. Otherwise, it is possible to treat it outside the reactor with carbon monoxide and hydrogen together with an organic phosphorus compound ligand in a solvent at a high temperature and pressure to preliminarily obtain a catalyst solution. The solvent for the preparation of this catalyst solution is usually selected from the reaction solvents which will be described hereinafter. However, it may or may not be the same as the solvent for reaction. With respect to the preparation conditions, it is usual to conduct the reaction at a rhodium concentration of from a few ppm to few % by weight at a molar ratio of the trivalent organic phosphorus compound ligand to rhodium of P/Rh=10 to 10,000 at a temperature of from 60° to 200° C. under a pressure of from atmospheric pressure to 200 kg/cm$^2$G for a treating time within a range of from a few minutes to ten-odd hours.

The above treatment may be conducted in a batch system or in a continuous system.

As the solvent for the hydroformylation reaction, the olefin itself may be used as the solvent, or it is possible to use the formed aldehyde or HB formed as a by-product. Further, it is possible to employ a solvent which is capable of dissolving the catalyst and which does not adversely affect the reaction, such as an aliphatic hydrocarbon such as hexane or octane, an aromatic hydrocarbon such as toluene or xylene, an alicyclic hydrocarbon such as cyclohexane, an alcohol such as butanol, octanol, polyethylene glycol or polypropylene glycol, an ether such triglyme or tetraglyme, an ester such as dioctyl phthalate, or water. With respect to the reaction conditions, the hydroformylation is conducted usually under a hydrogen partial pressure of from 0.1 to 200 kg/cm$^2$G, under a carbon monoxide partial pressure of from 0.1 to 200 kg/cm$^2$G, under a total pressure of from a few kg/cm$^2$G to 300 kg/cm$^2$G, at a ratio of hydrogen partial pressure/carbon monoxide partial pressure=0.1 to 10, at a temperature of from 60° to 200° C., at a rhodium concentration of from a few ppm to a few % by weight, a ratio of P/rhodium in the trivalent organic phosphorus compound ligand=10 to 10,000 (molar ratio) for a reaction time within a range of from a few minutes to ten-odd hours.

In the present invention, two reactor systems having different mixing characteristics are used in combination.

Namely, the first stage reactor system comprises a reactor or reactors wherein the mixing characteristic of the liquid phase is of substantially complete mixing type, and the second stage reactor system is a reaction system of catalyst solution circulating type and comprises a reactor or reactors having a mixing characteristic of piston flow type wherein when the mixing characteristic of the liquid phase is represented by a diffusion model, the flow mixing parameter U is at least 0.4. A gaseous product or a gas-liquid mixture discharged from the first stage reactor system is separated into a stream containing the unreacted olefin and other stream, and a part or whole of the stream containing the unreacted olefin is supplied to the second stage reactor system.

The mixing characteristic of the liquid phase of the above reactor or reactors can be represented by the flow mixing parameter U expressed by means of the diffusion model as described hereinafter. Accordingly, in the process of the present invention, the mixing characteristic of the liquid phase in the reactor system is expressed by the value of parameter U as represented by a diffusion model.

According to Yagi et al. (Chemical Engineering, vol. 17, No. 10, P.382–386(1953)), the mixing characteristic in a diffusion model can be quantitatively analyzed by a tracer test by a pulse response method.

Namely, the relation between the residence time in the reactor of a fluid discharged from the reactor and the discharge frequency (the E($\phi$) function by Danckwerts) can be expressed as follows.

Namely, by means of a non-demensional number U ("flow mixing parameter") defined by the formula:

$$U = \bar{u}L/2\bar{E} \tag{I}$$

wherein $\bar{u}$ is an average flow velocity (cm/sec), L is the length (cm) of the reaction layer, and $\bar{E}$ is an average diffusion coefficient (cm$^2$/sec), $$E(\phi) = 2 \sum_{n=1}^{\infty} \frac{\mu_n (U \sin \mu_n + \mu_n \cos \mu_n)}{(U^2 + 2U + \mu_n^2)} \tag{II}$$

$$\exp\left(U - \left[\frac{U^2 + \mu_n^2}{2U}\right]\phi\right)$$

here, $\mu_n$ is the nth root of:

$$\cot \mu = \frac{1}{2}\left[\frac{\mu}{U} - \frac{U}{\mu}\right]$$

Figure 5:
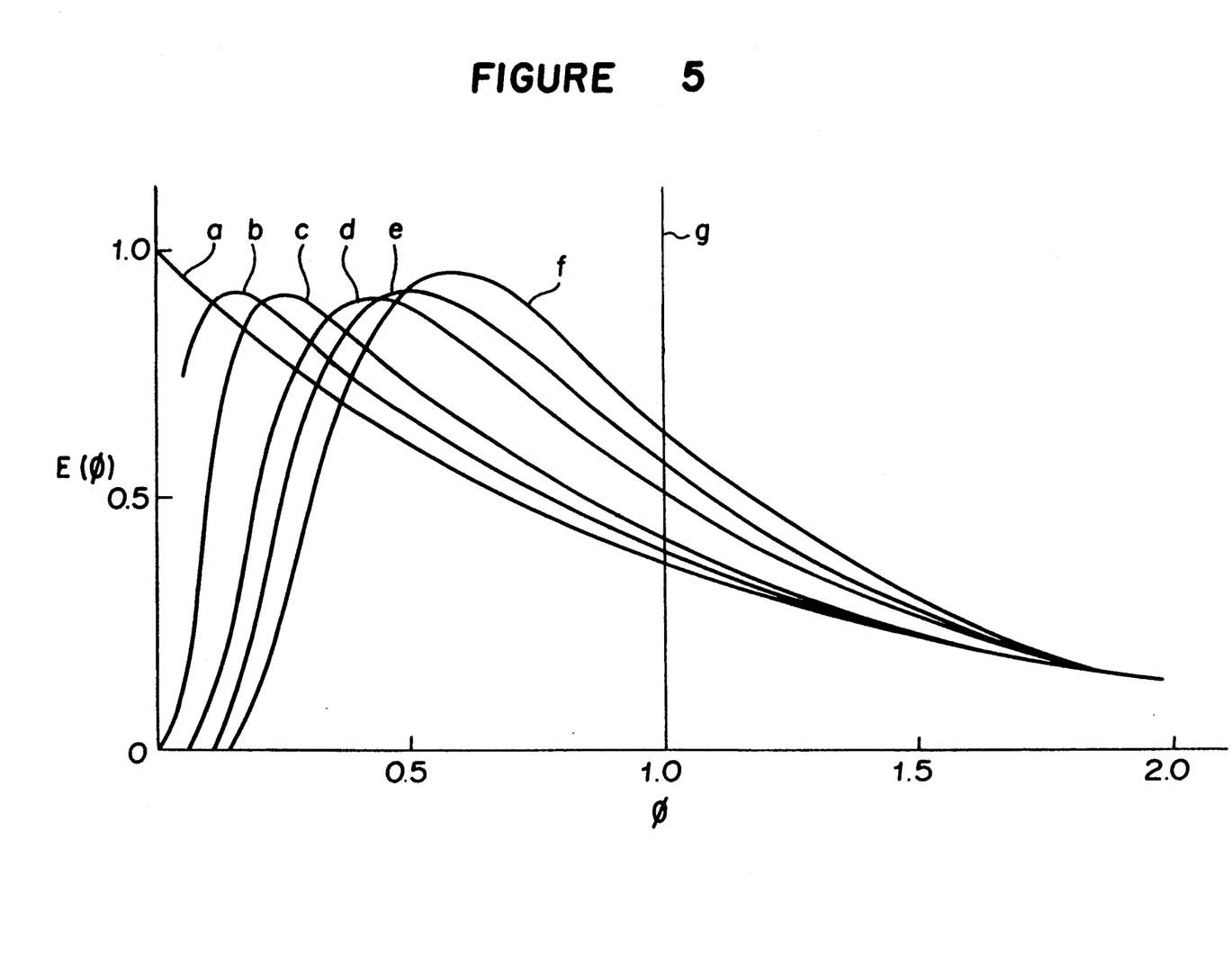
FIG. 5 is a graph showing the relation of $E(\phi)$-$\phi$ with U being a parameter of the following Formula (II).

With respect to the formula (II), if E($\phi$) is plotted against $\phi$ including U as parameter, FIG. 5 is obtained, whereby U=0 corresponds to ideal complete mixing, and U=∞ corresponds to ideal piston flow. In FIG. 5, a corresponds to U=0, b corresponds to U=0.2, c corresponds to U=0.4, d corresponds to U=1.0, e corresponds to U=1.4, f corresponds to U=2.0, and g corresponds to U=∞. Therefore, if the response data of a tracer test are standardized and compared with FIG. 5, the value U can be obtained. For the standardization, the tracer test data are plotted as is well known to obtain a smooth response curve, whereby from $$\bar{t} = \Sigma(t \cdot C_w)/\Sigma C_w \tag{III}$$

$$\phi = t/\bar{t} \tag{IV}$$

and from $$E(t) = C_w/\Sigma C_w \cdot \Delta t \tag{V}$$

$$E(\phi) = \bar{t} \cdot E(t) \qquad (VI)$$

wherein t is the measuring time (hr), $C_w$ is the tracer concentration at the measuring time t, $\Delta t$ is the allowance in reading the time (hr), and $\bar{t}$ is the average residence time (hr).

The tracer is preferably the one which is not present in the system and which does not change by the reaction. For example, it may be a paraffinic hydrocarbon not contained in the raw materials, a solvent not used for the reaction system or an oxide of an organic phosphorus compound not used in the reaction system.

In the first reactor system in the present invention, a reactor wherein the mixing characteristic of the liquid phase is substantially of complete mixing type is used alone, or a plurality of such reactors are used in parallel or in series. The characteristic substantially of complete mixing type means that the flow mixing parameter U of the formula (I) is less than 0.4. U is preferably not higher than 0.3.

The structure of the reactor having a complete mixing characteristic is known and is usually an agitation tank provided with a stirrer. However, if the flow rate of gas is large, a substantially complete mixing characteristic can be obtained by the stirring effects of the gas.

The whole of the olefin raw material and a part or whole of a gas mixture (hereinafter referred to as an oxo gas) of hydrogen and carbon monoxide, are fed to this first stage reactor system. The reaction system may be a catalyst solution circulating system wherein the catalyst solution is withdrawn out of the reactor together with the product, or a so-called gas stripping system wherein the product is distilled in the form of a gas while confining the catalyst solution in the reactor.

The gas-liquid mixture discharged from the first reactor system, or in the case of the stripping system, a gaseous product, is cooled as the case requires and then separated into a stream containing the unreacted olefin and other stream i.e. a stream containing the formed aldehyde. The separation method differs depending on e.g. the boiling point of the olefin. However, the separation is conducted usually by a conventional method such as distillation or stripping by means of a gas. In such a case, if necessary, the separation of a gas component composed essentially of the oxo gas may be conducted prior to the separation of the unreacted olefin. A part or whole of the gas component composed essentially of the oxo gas and the separated unreacted olefin, is fed to the second stage reactor system, and the rest is recycled to the first stage reactor system.

The stream containing the formed aldehyde is subjected to separation of the formed aldehyde from other components by a conventional method such as distillation. In a case where the other components contain the catalyst as in the case of the catalyst solution circulating system, such other components can be recycled as a catalyst solution to the first stage reactor system. In such a case, the aldehyde separation step may be combined with the second stage aldehyde separation step, as will be described hereinafter.

Further, a certain amount of olefin which was not separated in the previous step for separation of the unreacted olefin, may sometimes be recovered by this aldehyde separation. The recovered olefin is usually recycled to the first stage reactor system, but it may be fed to the second stage reactor system.

The second stage reactor system is a reaction system in which a reactor of a catalyst solution circulating type is used alone or a plurality of such reactors are used in parallel and/or in series, and the mixing characteristic of the liquid phase in each reactor is a piston flow type mixing characteristic where the flow mixing parameter $U \geq 0.4$, preferably $U \geq 0.5$. There is no particular restriction as to the upper limit ($U = \infty$). For the industrial purpose, however, U is usually within a range of from 0.4 to 100, preferably from 0.5 to 50.

Construction of such a reactor can be made by a conventional method, for example, by providing a plurality of perforated partitions to a cylindrical reactor, or by using a pipe reactor and increasing the liquid linear speed.

The unreacted olefin and oxo gas discharged from the first stage reactor system and, if necessary, an additional oxo gas raw material, are fed together with the circulating catalyst solution to the second stage reactor system.

The ratio of the unreacted olefin to the circulating catalyst solution is not particularly critical, but it is usually as follows:

Unreacted olefin/circulating catalyst solution = 0.01 to 5

(weight flow ratio)

Preferably the ratio is within a range of from 0.01 to 1.

In a case where a catalyst solution circulating system is employed as the first reactor system, the ratio of the raw material olefin to be fed to the circulating catalyst solution is usually as follows:

Low material olefin/circulating catalyst solution = 0.01 to 5

(weight flow ratio)

The ratio is preferably within a range of from 0.01 to 1.

The gas-liquid mixture discharged from the second stage reactor system is, if necessary, cooled and then separated into a gas and a liquid containing the formed aldehyde and the catalyst. The gas is purged, but a part thereof may be recycled to the second stage reactor system.

From the liquid containing the formed aldehyde and the catalyst, the formed aldehyde is separated by a conventional method such as distillation, and the catalyst solution is recycled to the second stage reactor system.

Further, the first stage aldehyde separation step and the second stage aldehyde separation step may be conducted by the same apparatus.

In such a case, the stream after separation of the unreacted olefin of the first stage is combined with the stream before or after the gas separation of the second stage, and if necessary after being subjected to gas separation, the mixture is separated into the aldehyde and the catalyst solution, whereupon the catalyst solution is recycled to the second stage reactor system, but a part thereof may be recycled also to the first stage reactor system.

A part of the circulating catalyst solution is withdrawn, and HB is separated by a known method such as distillation, crystallization or extraction, and the catalyst component may be recovered and combined to the circulating catalyst solution for reuse.

In the present invention, the first stage reactor system has a characteristic of substantially complete mixing type, and the concentration distribution in the liquid is not substantially present, whereby the reaction can be conducted under the optimum one point reaction condition, and accordingly the yield of LB and HB can be minimized. If this reaction is conducted by a reactor system having a mixing characteristic of piston flow type, a concentration distribution will necessarily be formed in the reactor, and accordingly, the reaction is conducted under a relatively wide range of condition, whereby the optimization of the reaction tends to be difficult. In the reactor having a complete mixing characteristic, there is a limit in reducing the concentration of the olefin. The concentration of the olefin and the volume of the reactor are inversely proportional. Therefore, from the industrial and economical viewpoint, it is unavoidable to permit a substantial amount of unreacted olefin. This problem becomes serious particularly when the purity of the raw material olefin is low. Namely, as accompanied with the purge to prevent accumulation of impurities, the olefin is likely to be lost unnecessarily.

Thus, in order to efficiently convert the unreacted olefin, the second stage reactor system is essential.

The second stage reactor system is designed so that the aldehyde formed in the first stage reactor system will not substantially be fed to the second stage reactor system.

As is well known, the aldehyde is usually highly reactive and unstable. Accordingly, if it is fed to the second stage reactor system, it is likely to undergo polycondensation by the heat in the reactors to form HB, whereby it is impossible to minimize the yield of HB.

If a complete mixing type is employed for the second stage reactor system, it is difficult to minimize the amount of the unreacted olefin for the same reason as described with respect to the first stage reactor system. Therefore, as the second stage reactor system, it is preferred to employ a reaction system having a mixing characteristic of piston flow type. With a piston flow type reactor having a mixing characteristic with a flow mixing parameter $U \geq 0.4$, it is possible to reduce the amount of the unreacted olefin at the outlet to an extremely small level. A certain concentration distribution exists in the reactor. Accordingly, it is here not possible to minimize the yield of LB and HB. However, by adjusting U at a level of at least 0.4 depending upon the reaction rate of the second stage, it is possible to be substantially harmless for minimizing the yield of LB and HB as a total of the first and second stages. Namely, when the reaction rate in the second stage is small, the value for U of the second stage may be set at a relatively large value over 0.4, and when the reaction rate in the second stage is large, the value for U at the second stage is set at a relatively small level of at least 0.4, whereby the yield of LB and HB can be minimized as a total of the first and second stages.

The molar ratio of the conversion of the olefin in the second stage reactor system to the conversion of the olefin in the first stage reactor system is usually at least 1, preferably at least 0.5, more preferably at least 0.3. From the industrial point of view, the molar ratio is within a range of from 0.01 to 1, preferably from 0.01 to 0.5, more preferably from 0.03 to 0.2.

Now, the present invention will be described in further detail with reference to Examples. However, it should be understood that the present invention is by no means restricted to such specific Examples.

EXAMPLE 1

Figure 1:
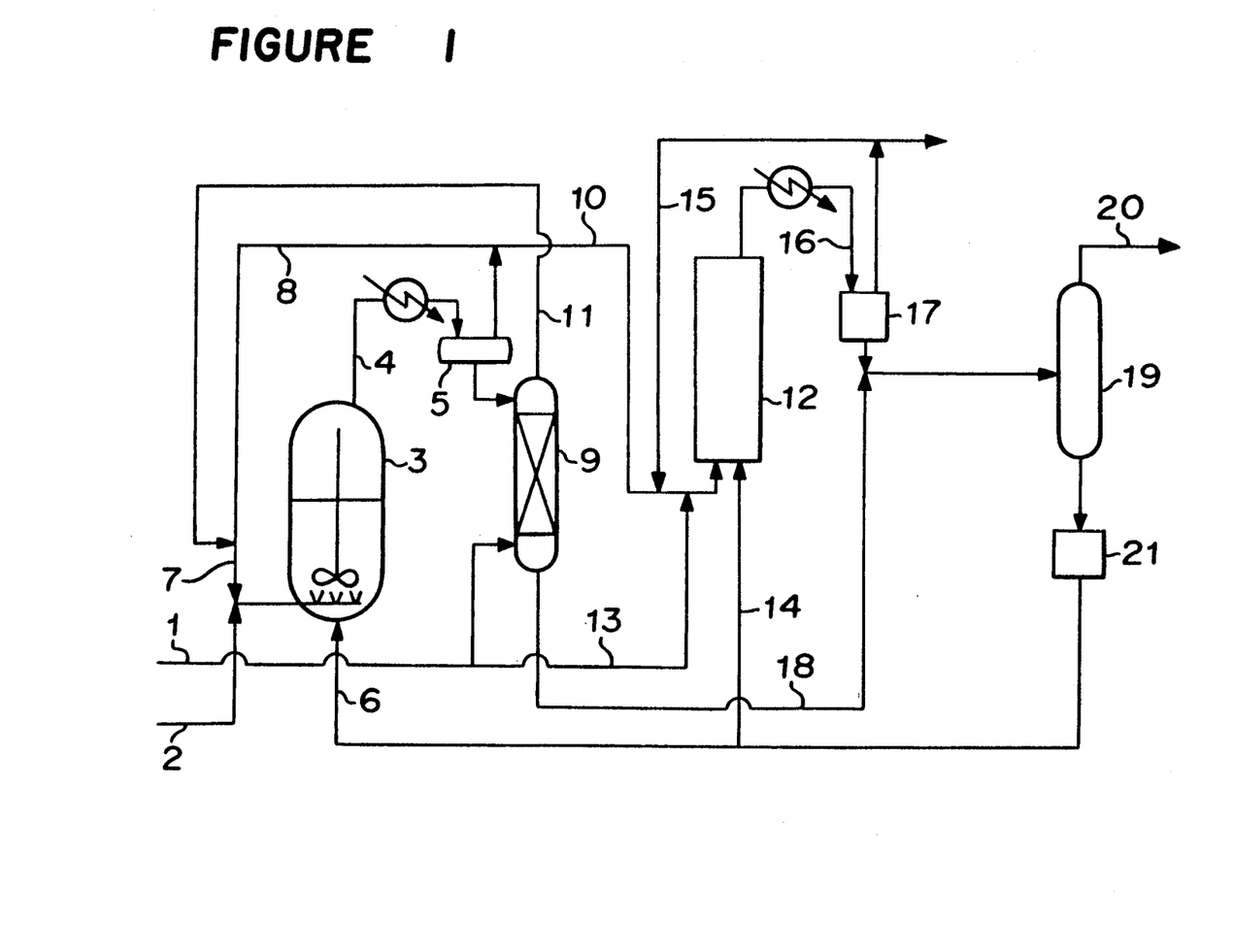
FIG. 1 is a flow diagram illustrating the hydroformylation process in Example 1 according to the present invention.

In accordance with the flow diagram shown in FIG. 1, a hydroformylation reaction of propylene was conducted using the raw materials and the catalyst solution as identified in the following item (1) under the reaction conditions as identified in the following item (2).

(1) Raw materials and catalyst solution

| Raw materials: | | |
|---|---|---|
| Propylene purity: | Propane | 3.5 mol % |
| | Propylene | 96.5 mol % |
| Oxo gas purity: | $H_2$ | 50.23 mol % |
| | CO | 49.77 mol % |

Catalyst solution

A rhodium hydridocarbonyltris(triphenyl phosphine) complex was dissolved in p-xylene so that triphenyl phosphine would be 15 wt % and rhodium would be 200 ppm.

(2) Reaction conditions

| First stage reactor system: | |
|---|---|
| Reaction temperature | 100° C. |
| Total pressure | 18 kg/cm² G |
| $H_2$/CO | 1.5 |
| Liquid residence time (Empty column base) | About 3.0 hours |
| Second stage reactor system: | |
| Reaction temperature | 90° C. |
| Total pressure | 16 kg/cm² G |
| $H_2$/CO | 2.0 |
| Liquid residence time (Empty column base) | About 2.0 hours |
| Feeding amounts: | |
| Raw material propylene | 4 mol/hr |
| Raw material oxo gas | 7.8 mol/hr |

The first stage reactor system employed one agitation tank reactor 3, the entire amount of propylene was fed from a pipe to the bottom. 88% of the entire amount of fresh oxo gas and recycling gas were fed from a pipe 7. Further, a circulating catalyst solution was fed from a pipe 6 at a ratio of propylene/circulating catalyst solution=0.18 (weight flow ratio).

The reaction product solution was withdrawn by a pipe 4 by over flow in a gas-liquid mixed phase, then cooled to 80° C. and subjected to gas-liquid separation at a gas-liquid separator 5, whereupon the gas was adjusted so that the empty column base GLV became 20 m/H and recycled by a pipe 8, and the rest was fed by a pipe 10 to a second stage reactor system. In the liquid after the gas-liquid separation, a substantial amount of the unreacted propylene was dissolved. Therefore, the liquid was subjected to gas stripping at a gas stripping column 9 with about 88% of the total amount of fresh oxo gas from a pipe 1, whereby the total amount of the propylene dissolved in the liquid was recovered and recycled via pipes 11 and 7 to the first stage reactor system. As the gas stripping column 9, a packed column having a height of 5 m was used.

The second stage reactor system comprised one cylindrical bubbling column reactor 12 provided internally with ten perforated partitions and no stirrer. The feed gas from the first stage reactor system (via a pipe 10), oxo gas corresponding to about 12% of the total amount of fresh oxo gas (via a pipe 13), recycling gas (via a pipe 15) and a circulating catalyst solution (via a pipe 14) at a weight flow ratio of propylene (in the pipe 10)/circulating catalyst solution=0.2 were fed.

The reaction product solution was a gas-liquid mixed phase, was cooled to 60° C. and then via a pipe 16, subjected to gas-liquid separation at a gas-liquid separator 17, whereupon a predetermined amount of the gas was adjusted so that an empty column base GLV at the inlet of the reactor became 20 m/hr and recycled by a pipe 15, and the rest of the gas was purged.

The liquid after the gas-liquid separation was combined with the liquid of the first stage reactor system after the propylene stripping with oxo gas (a pipe 18), and the combined liquid was separated at the distillation column 19 into the product aldehyde (a pipe 20) and the catalyst solution. The catalyst solution was recycled via a catalyst drum 21 to the first stage reactor system and to the second stage reactor system.

The reaction was conducted continuously for four days.

The reaction conditions were stabilized from the second day to present constant results, and no deterioration in the activity was observed. The average values during the three days of from the second day to the fourth day are shown below.

The analysis of the product was conducted by means of gas chromatography.

The analysis of HB was conducted by gas chromatography up to the trimer of aldehyde, and for the tetramer or higher polymer, gel permeation chromatography was employed.

① Overall reaction results

| | |
|---|---|
| Propylene conversion | 99.0% |
| Conversion to LB (propane) | 0.54% |
| Conversion to HB | 0.39% |
| Yield of aldehyde (butyraldehyde) | 98.07% |
| Molar ratio of n-butyraldehyde/i-butyraldehyde (hereinafter referred to simply as n/i) | 11.1 |

② Reaction results at the first stage reactor system

| | |
|---|---|
| Propylene conversion | 88.0% |
| Conversion to LB (propane) | 0.44% |
| Selectivity for LB (propane) | 0.5% |
| Conversion to HB | 0.34% |
| Selectivity for HB | 0.39% |
| Yield of aldehyde | 87.22% |
| Selectivity for aldehyde | 99.1% |
| n/i | 11.0 |

③ Reaction results at the second stage reactor system

| | |
|---|---|
| Propylene conversion (to the total) | 11.0% |
| Conversion to LB (propane) | 0.10% |
| Selectivity for LB (propane) | 0.91% |
| Conversion to HB | 0.05% |
| Selectivity for HB | 0.45% |
| Yield of aldehyde | 10.85% |
| Selectivity for aldehyde | 98.6% |
| n/i | 11.9 |

The selectivity for propane in the second stage reactor system is slightly poor as compared with the first stage reactor system. However, there was no adverse effect to the overall reaction results.

Further, the following tracer test was conducted with respect to this reactor system to obtain a flow mixing parameter U.

(3) Tracer test n-Hexane was used as a tracer, and it was fed for three minutes at a flow rate of 1/10 (weight flow ratio) of the flow rate of the circulating catalyst solution, to the circulating catalyst line immediately prior to the inlet of the reactor, and the change with time of the concentration of n-hexane was observed at the outlet of the reactor by gas chromatography. Firstly, the measurement was conducted with respect to the second stage reactor system.

Figure 3:
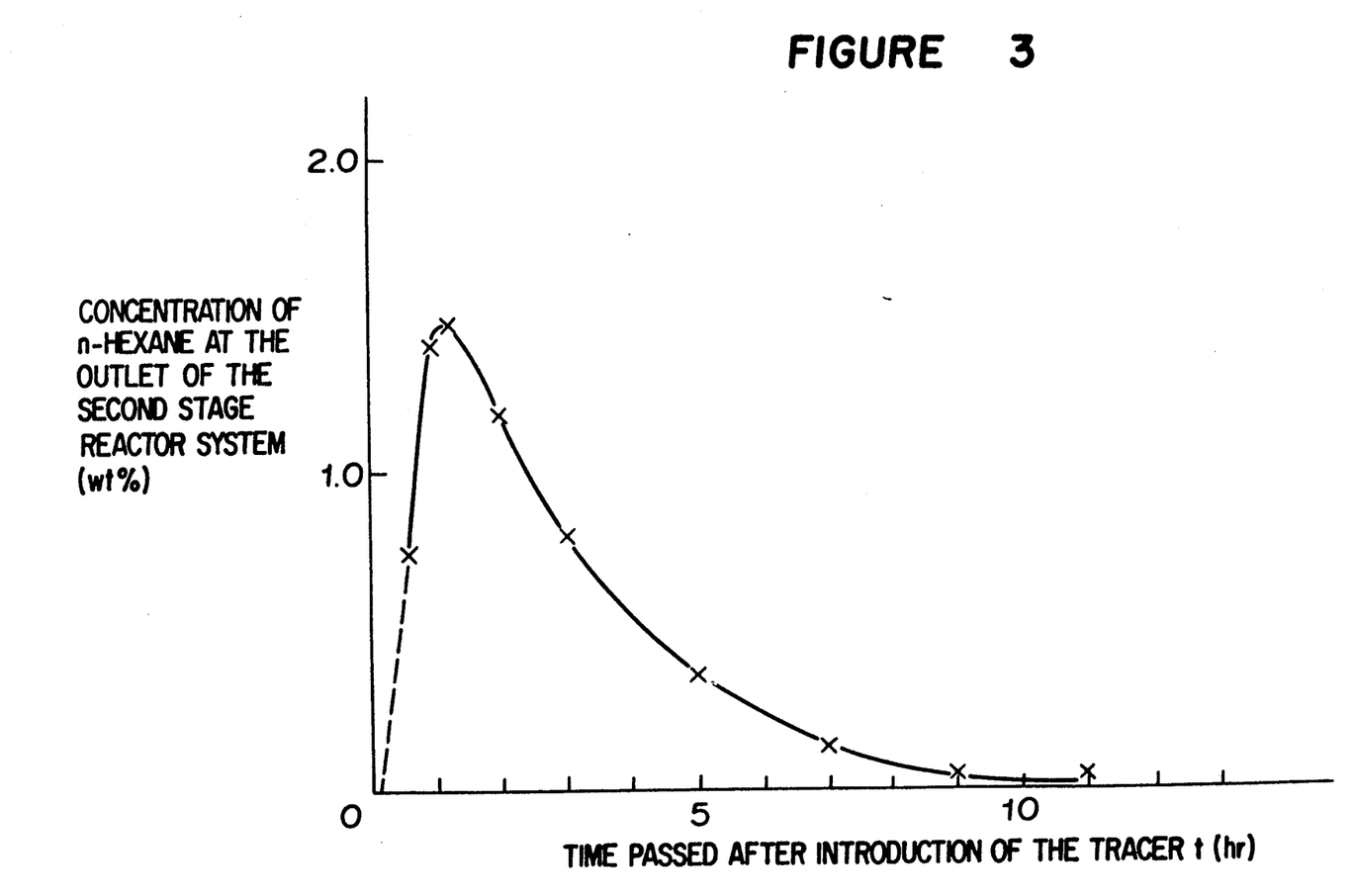
FIG. 3 is a graph showing the response curve in the tracer test of the second stage reactor system of the hydroformylation process in Example 1 according to the present invention.

With the completion of the introduction of the tracer being 0 time, a response curve was drawn with the ordinate representing the n-hexane concentration (wt %) at the outlet of the second stage reactor system and the abscissa representing the time t (hr) passed after the introduction of n-hexane, whereby FIG. 3 was obtained.

Figure 4:
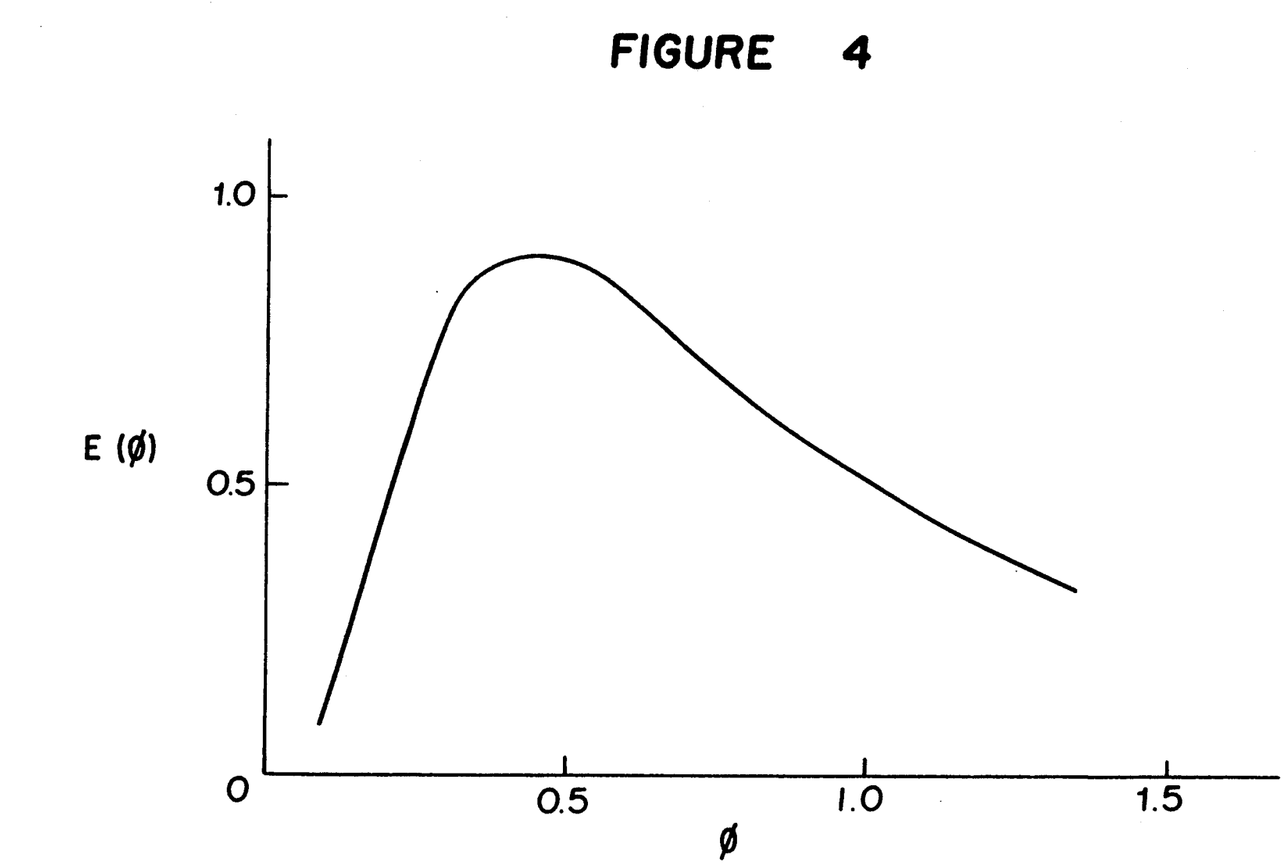
FIG. 4 is a graph showing the relation of $E(\phi)$-$\phi$ in the second reactor system of the hydroformylation process in Example 1 according to the present invention.

This was standardized by means of the above formulas (III) to (VI) from 0.4 hour later to 11 hour later with a width of $\Delta t = 0.2$ hour, and plotted with the ordinate representing $E(\phi)$ and with the abscissa representing $\phi$ to obtain FIG. 4. This FIG. 4 was compared with FIG. 5, whereby $U = 1.0$ was found. In a similar manner, a tracer test was conducted with respect to the first stage reactor system, whereby $U = 0.15$ was found.

EXAMPLE 2

The operation was conducted in the same manner as in Example 1 except that the reaction temperature of the second stage reactor system and the first stage reactor system was 95° C., and the number of partitions in the bubbling column of the second stage reactor system was changed to 15 sheets.

The reaction results are as follows.

① Overall reaction results

| | |
|---|---|
| Propylene conversion | 99.3% |
| Conversion to LB (propane) | 0.58% |
| Conversion to HB | 0.31% |
| Yield of aldehyde | 98.41% |
| n/i | 10.9% |

② Reaction results at the first stage reactor system

| | |
|---|---|
| Propylene conversion | 70.3% |
| Conversion to LB | 0.29% |
| Selectivity for LB | 0.42% |
| Conversion to HB | 0.14% |
| Selectivity for HB | 0.20% |
| Yield of aldehyde | 69.87% |
| Selectivity for aldehyde | 99.4% |
| n/i | 10.9 |

③ Reaction results at the second stage reactor system

| | |
|---|---|
| Propylene conversion | 29.0% |
| Conversion to LB | 0.29% |
| Selectivity for LB | 1.0% |
| Conversion to HB | 0.17% |
| Selectivity for HB | 0.6% |
| Yield of aldehyde | 28.54% |
| Selectivity for aldehyde | 98.4% |
| n/i | 11.0 |

Further, the results of the same tracer tests as in Example 1 were as follows:
First stage reactor system $U = 0.14$
Second stage reactor system $U = 1.7$

EXAMPLE 3

Figure 2:
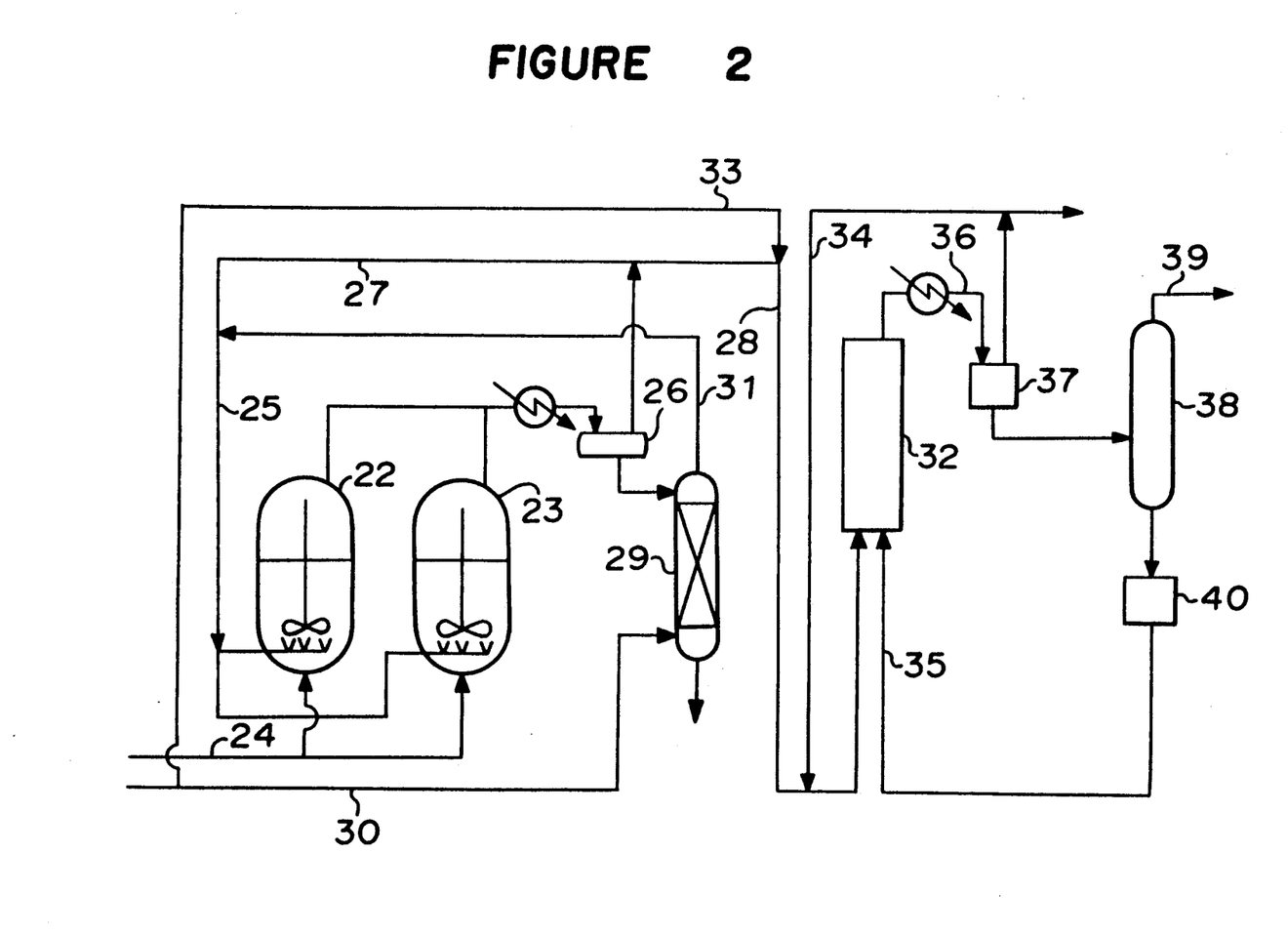
FIG. 2 is a flow diagram illustrating the hydroformylation process in Example 3 according to the present invention.

In accordance with the flow diagram shown in FIG. 2, a hydroformylation reaction of propylene was conducted using the raw materials and the catalyst solution as identified in the following item (1) under the reaction conditions as identified in the following item (2).

(1) Raw materials and catalyst solution

The raw material propylene and oxo gas were the same as in Example 1. For the second stage reactor system, the catalyst solution was exactly the same as used in Example 1.

For the first reactor system, a HB solution was prepared as follows:

Namely, to n-butyraldehyde, 5 wt % triphenyl phosphine was added, and the mixture was heat-treated at 120° C. for 20 days under nitrogen. Twenty days later, this solution was analyzed by gas chromatography, whereby remaining n-butyraldehyde was 3.2 wt %, 27.4 wt % was found to be the dimer of n-butyraldehyde, and 60 wt % was found to be the trimer (others: 9.4 wt %).

To this HB solution, triphenyl phosphine and rhodium hydridocarbonyltris(triphenyl phosphine) complex was added to obtain a catalyst solution containing 14.0 wt % of triphenyl phosphine and 420 ppm by weight of rhodium.

(2) Reaction conditions

| First stage reactor system: | |
| --- | --- |
| Reaction temperature | 100° C. |
| Total pressure | 17 kg/cm$^2$ G |
| H$_2$/CO | 1.5 |
| Second stage reactor system: | |
| Reaction temperature | 90° C. |
| Total pressure | 15 kg/cm$^2$ G |
| H$_2$/CO | 2.1 |
| Residence time (Empty column base) | About 2.0 hours |
| Feeding amounts: | |
| Raw material propylene | 4 mol/hr |
| Raw material oxo gas | 7.8 mol/hr |

The first stage reactor system comprised two reactors each with a capacity of ½ of the first stage reactor in Example 1, disposed in parallel to each other (agitation tank reactors 22 and 23).

The raw material propylene (a pipe 24), and 88% of the total amount of fresh oxo gas and recycle gas (a pipe 25) were fed in equal amounts to the respective reactors. The product aldehyde, LB and HB were subjected to gas stripping, and the liquid surface in each reactor was maintained at a predetermined level. The catalyst solution was retained in the reactors 22 and 23 in a confined system.

Namely, the gaseous product streams at the outlet of the first stage reactor system were joined together and cooled to 70° C. Then, the cooled product was subjected to gas-liquid separation in a gas-liquid separator 26, whereupon a predetermined amount of the gas required for stripping the product, was recycled by a pipe 27, and the rest was fed via a pipe 28 to the second stage reactor system.

In the liquid after the gas-liquid separation, a substantial amount of unreacted propylene was dissolved. Therefore, in the same manner as in Example 1, it was subjected to gas stripping by a gas stripping column 29 with about 88% of the total amount of fresh oxo gas from a pipe 30, to recover all the amount of propylene dissolved in the liquid, and the recovered propylene was recycled to the first stage reactor system via a pipe 31 and a pipe 25. The gas stripping column 29 was a packed column having a height of 5 meters.

The second stage reactor system was the same as used in Example 1.

Namely, to a bubbling column 32 the feed gas from the first stage reactor system (a pipe 28) and oxo gas corresponding to about 12% of the total amount of fresh oxo gas (a pipe 33), a recycling gas (a pipe 34) and a circulating catalyst solution (a pipe 35) having a weight flow rate of propylene in a pipe 28/circulating catalyst solution=0.2 were fed.

The reaction product solution was a gas-liquid mixed phase, and it was cooled to 60° C. and then subjected to gas-liquid separation by a gas-liquid separator 37 via a tube 36, whereupon a predetermined amount of the gas was recycled by a pipe 34 so that the empty column base GLV in the reactor became 20 m/hr, and the rest of the gas was purged.

The liquid after the gas-liquid separation was separated by a distillation column 38 into the product aldehyde (a pipe 39) and the catalyst solution, and the catalyst solution was recycled to the second stage reactor system via a catalyst drum 40.

The reaction was conducted continuously for three days.

The reaction results were completely stabilized from the second day, and no deterioration in the activity was observed. The average results during the two days from the second day to the third day are shown below.

| ① Overall reaction results | |
| --- | --- |
| Propylene conversion | 98.9% |
| Conversion to LB | 0.57% |
| Conversion to HB | 0.40% |
| Yield of aldehyde | 97.9% |
| n/i | 11.72 |
| ② Reaction results at the first stage reactor system | |
| Propylene conversion | 80.5% |
| Conversion to LB | 0.39% |
| Selectivity for LB (propane) | 0.48% |
| Conversion to HB | 0.32% |
| Selectivity for HB | 0.4% |
| Yield of aldehyde | 79.79% |
| Selectivity for aldehyde | 99.1% |
| n/i | 11.6 |
| ③ Reaction results at the second stage reactor system | |
| Propylene conversion | 18.4% |
| Conversion to LB | 0.18% |
| Selectivity for LB | 0.98% |
| Conversion to HB | 0.08% |
| Selectivity for HB | 0.41% |
| Yield of aldehyde | 18.1% |
| Selectivity for aldehyde | 98.6% |
| n/i | 12.3 |

(3) Tracer test

A tracer test was conducted in the same manner as in Example 1, whereby the results are as follows:
First stage reactor system U=0.13
(substantially the same in both reactors)
Second stage reactor system U=1.2

EXAMPLE 4

The operation was conducted in the same manner as in Example 1 except that the number of partitions in the bubbling column in the second stage reactor system was changed to 5 sheets.

The reaction results were as follows.

| ① Overall reaction results | |
| --- | --- |
| Propylene conversion | 98.5% |
| Conversion to LB | 0.53% |
| Conversion to HB | 0.38% |
| Yield of aldehyde | 97.59% |
| n/i | 11.1 |
| ② Reaction results at the first stage reactor system | |

| -continued | |
|---|---|
| Propylene conversion | 88.0% |
| Conversion to LB | 0.44% |
| Selectivity for LB | 0.5% |
| Conversion to HB | 0.34% |
| Selectivity for HB | 0.39% |
| Yield of aldehyde | 87.22% |
| Selectivity for aldehyde | 99.1% |
| n/i | 11.0 |
| ③ Reaction results at the second stage reactor system | |
| Propylene conversion | 10.5% |
| Conversion to LB | 0.09% |
| Selectivity for LB | 0.86% |
| Conversion to HB | 0.04% |
| Selectivity for HB | 0.38% |
| Yield of aldehyde | 10.37% |
| Selectivity for aldehyde | 98.76% |
| n/i | 11.5 |

A tracer test was conducted in the same manner as in Example 1, whereby the following results were obtained:
First stage reactor system $U=0.15$
Second stage reactor system $U=0.5$

COMPARATIVE EXAMPLE 1

The operation was conducted in exactly the same manner as in Example 1 except that for the second stage reactor system, an agitation tank reactor having the same volume as the bubbling column reactor used for the second stage reactor system in Example 1, was used.
Results of the tracer test:
First stage reactor system $U=0.15$
Second stage reactor system $U=0.15$
The reaction results were as follows:

| ① Overall reaction results | |
|---|---|
| Propylene conversion | 96.9% |
| Conversion to LB | 0.49% |
| Conversion to HB | 0.38% |
| Yield of aldehyde | 96.1% |
| n/i | 11.1 |
| ② Reaction results at the first stage reactor system | |
| Propylene conversion | 88.0% |
| Conversion to LB | 0.44% |
| Selectivity for LB | 0.5% |
| Conversion to HB | 0.34% |
| Selectivity for HB | 0.39% |
| Yield of aldehyde | 87.22% |
| Selectivity for aldehyde | 99.1% |
| n/i | 11.0 |
| ③ Reaction results at the second stage reactor system | |
| Propylene conversion | 8.9% |
| Conversion to LB | 0.044% |
| Selectivity for LB | 0.5% |
| Conversion to HB | 0.035% |
| Selectivity for HB | 0.4% |
| Yield of aldehyde | 8.8% |
| Selectivity for aldehyde | 99.0% |
| n/i | 11.4 |

As compared with Example 1, the amount of the unreacted propylene shows a significant difference, indicating poor efficiency.

Figure 6:
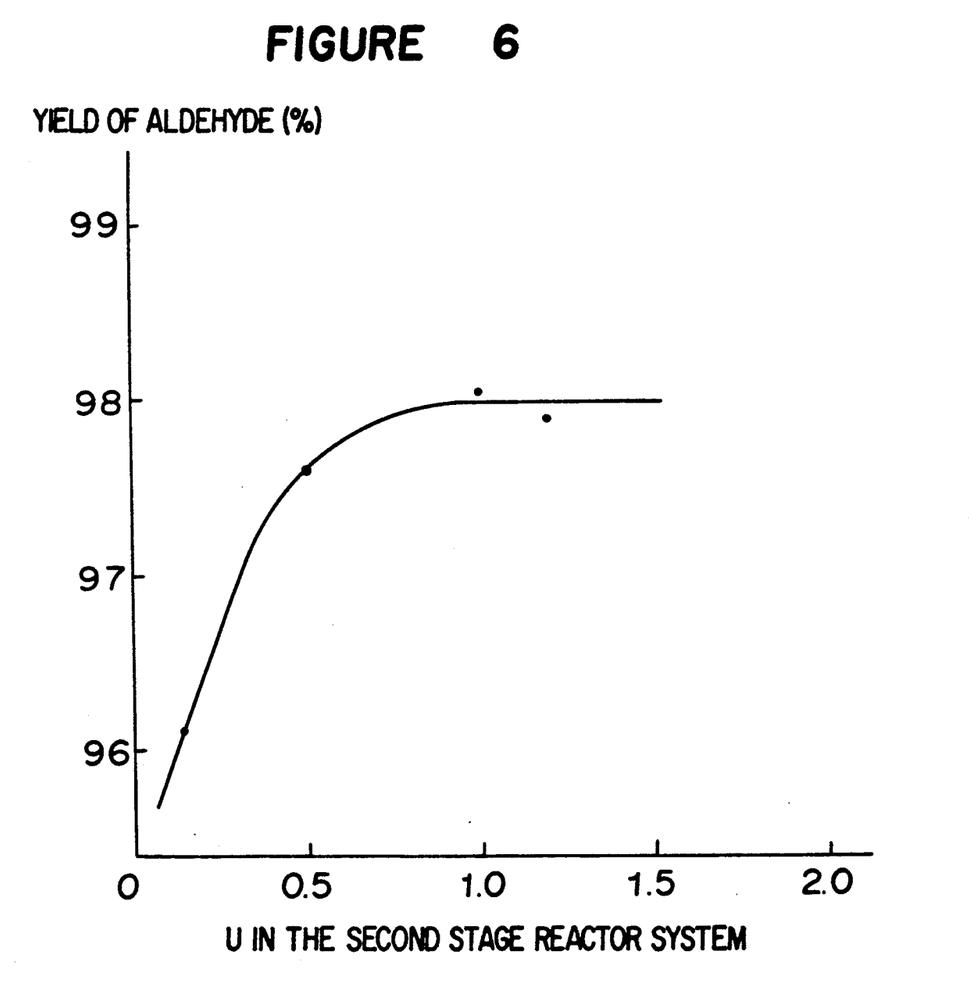
FIG. 6 is a graph obtained by plotting the relation between the U value of the second stage reactor system and the yield of aldehyde at the outlet of the second reactor system from the results of Examples 1, 3 and 4 and Comparative Example 1.

From the results of Examples 1, 3 and 4 and Comparative Example 1, the relation between the U value of the second stage reactor system and the yield of aldehyde at the outlet of the second stage reactor system was plotted to obtain the graph of FIG. 6. In Examples 1, 3 and 4 and Comparative Example 1, the U value of the first stage reactor system was constantly at a level of from 0.13 to 0.15. From FIG. 6, it is evident that when the U value of the second stage reactor system is at least 0.4, a high yield of aldehyde is obtainable while conversion to LB and HB can be minimized.

COMPARATIVE EXAMPLE 2

The operation was conducted in exactly the same manner as in Example 1 except that for the first stage reactor system, a cylindrical bubbling column reactor having the same volume as the first stage reactor in Example 1 and provided with 8 partitions, was employed.
Results of the tracer test:
First stage reactor system $U=1.1$
Second stage reactor system $U=0.7$
The reaction results were as follows:

| ① Overall reaction results | |
|---|---|
| Propylene conversion | 99.9% |
| Conversion to LB | 1.52% |
| Conversion to HB | 1.70% |
| Yield of aldehyde | 96.68% |
| n/i | 10.9 |
| ② Reaction results at the first stage reactor system | |
| Propylene conversion | 97.1% |
| Conversion to LB | 1.5% |
| Selectivity for LB | 1.54% |
| Conversion to HB | 1.68% |
| Selectivity for HB | 1.73% |
| Yield of aldehyde | 93.9% |
| Selectivity for aldehyde | 96.7% |
| n/i | 10.9 |
| ③ Reaction results at the second stage reactor system | |
| Propylene conversion | 2.8% |
| Conversion to LB | 0.017% |
| Selectivity for LB | 0.6% |
| Conversion to HB | 0.011% |
| Selectivity for HB | 0.4% |
| Yield of aldehyde | 2.77% |
| Selectivity for aldehyde | 98.9% |
| n/i | 11.5 |

The conversion of propylene increased, but the conversion at the first stage reactor system was so large that the concentration distribution at the inlet and the outlet was too wide and the conversion to LB substantially increased. Further, due to the increase of the concentration of aldehyde, the conversion to LB also increased.

COMPARATIVE EXAMPLE 3

The operation was conducted in exactly the same manner as in Example 1 except that for the first stage reactor system, the first stage reactor system of Comparative Example 2 was employed, and for the second stage reactor system, the second stage reactor system of Comparative Example 1 was employed.
Results of the tracer test:
First stage reactor system $U=1.1$
Second stage reactor system $U=0.15$
The reaction results were as follows:

| ① Overall reaction results | |
|---|---|
| Propylene conversion | 99.3% |
| Conversion to LB | 1.51% |
| Conversion to HB | 1.71% |
| Yield of aldehyde | 96.08% |
| n/i | 10.9 |
| ② Reaction results at the first stage reactor system | |

| -continued | |
|---|---|
| Propylene conversion | 97.1% |
| Conversion to LB | 1.5% |
| Selectivity for LB | 1.54% |
| Conversion to HB | 1.7% |
| Selectivity for HB | 1.75% |
| Yield of aldehyde | 93.9% |
| Selectivity for aldehyde | 96.7% |
| n/i | 10.9 |
| ③ Reaction results at the second stage reactor system | |
| Propylene conversion | 2.1% |
| Conversion to LB | 0.011% |
| Selectivity for LB | 0.5% |
| Conversion to HB | 0.013% |
| Selectivity for HB | 0.6% |
| Yield of aldehyde | 2.08% |
| Selectivity for aldehyde | 99.0% |
| n/i | 11.3 |

According to the present invention, the hydroformylation reaction is conducted by means of a specific combination of two reactor systems having different mixing characteristics, whereby the hydroformylation of an olefin can be efficiently conducted while suppressing the formation of by-products.

I claim:

1. A process for hydroformylation of an olefin to form an aldehyde, which comprises reacting an olefin with carbon monoxide and hydrogen in the presence of a rhodium catalyst having a trivalent organic phosphorus compound as a ligand, wherein the hydroformylation reaction is conducted by two stage reactor systems comprising a first stage reactor system comprising a reactor or reactors having a mixing characteristic of the liquid phase being substantially of complete mixing type, and a second stage reactor system of complete mixing type, and a second stage reactor system being a reaction system of catalyst solution-circulating type and comprising a reactor or reactors having a mixing characteristic of piston flow type wherein when the mixing characteristic of the liquid phase is represented by a diffusion model, a non-dimensional flow mixing parameter number U defined by the formula (I):

$$U = \bar{\mu} L / 2\bar{E} \qquad (I)$$

wherein $\mu$ is an average flow velocity (cm/sec), L is the length (cm) of the reaction layer, and $\bar{E}$ is an average diffusion coefficient (cm$^2$/sec), is at least 0.4, a gaseous product or gas-liquid mixture discharged from the first stage reactor system, is separated into a stream containing the unreacted olefin and other stream, and a part or whole of the stream containing the unreacted olefin is supplied to the second stage reactor system.

2. The process according to claim 1, wherein the olefin is an olefin having from 2 to 5 carbon atoms or a mixture of olefins having from 2 to 5 carbon atoms.

3. The process according to claim 1, wherein the trivalent organic phosphorus compound is selected from the group consisting of trialkyl phosphines, triaryl phosphines, tricycloalkyl phosphines, alkylaryl phosphines, cycloalkylaryl phosphines, alkylcycloalkyl phosphines and phosphites.

4. The process according to claim 1, wherein the trivalent organic phosphorus compound is the one multidentate to rhodium.

5. The process according to claim 4, wherein the multidentate organic phosphorus compound is (diphenylphosphino)propane.

6. The process according to claim 1, wherein the rhodium source is selected from the group consisting of rhodium complexes, organic salts, inorganic salts and oxides.

7. The process according to claim 4, wherein the multidentate organic phosphorus compound is the one represented by the formula:

wherein each of $R_1$, $R_2$, $R_3$ and $R_4$ is an alkyl group or an aryl group, and Y is a bivalent linking group selected from the group consisting of hydrocarbon groups, oxygen-containing hydrocarbon groups, sulfur-containing hydrocarbon groups and nitrogen-containing hydrocarbon groups.

8. The process according to claim 1, wherein the hydroformylation reaction is conducted in a solvent selected from the group consisting of the olefin itself, formed aldehyde, HB formed as a by-product, aliphatic hydrocarbons, aromatic hydrocarbons, alicyclic hydrocarbons, alcohols, ethers, esters and water.

9. The process according to claim 1, wherein the hydroformylation reaction is conducted under a total pressure of from a few kg/cm$^2$G to 300 kg/cm$^2$G at a temperature of from 60° to 200° C.

10. The process according to claim 1, wherein the first stage reactor system comprises one reactor or a plurality of reactors connected in series or in parallel.

11. The process according to claim 1, wherein the flow mixing parameter U of the reactor or reactors of the first stage reactor system is less than 0.4.

12. The process according to claim 11, wherein U of the reactor or reactors of the first stage reactor system is at most 0.3.

13. The process according to claim 1, wherein the reactor or reactors of the first stage reactor system are an agitation tank or tanks equipped with a stirrer.

14. The process according to claim 1, wherein the second stage reactor system comprises one reactor or a plurality of reactors connected in series or in parallel.

15. The process according to claim 1, wherein the flow mixing parameter U of the second reactor system is $0.4 \leq U \leq 100$.

16. The process according to claim 1, wherein U of the second stage reactor system is $50 \geq U \geq 0.5$.

17. The process according to claim 1, wherein the reactor or reactors of the second stage reactor system are a cylindrical reactor or reactors having a plurality of perforated partitions provided therein, or a pipe reactor or reactors.

18. The process according to claim 1, wherein the gaseous product or gas-liquid mixture discharged from the first stage reactor system is separated by distillation into a stream containing the unreacted olefin and other stream.

19. The process according to claim 1, wherein the molar ratio of the olefin conversion in the second stage reactor system to the olefin conversion in the first stage reactor system is at most 1.

20. The process according to claim 19, wherein the molar ratio of the olefin conversion is within a range of from 0.01 to 1.

21. The process according to claim 19, wherein the molar ratio of the olefin conversion is within a range of from 0.01 to 0.5.

22. The process according to claim 19, wherein the molar ratio of the olefin conversion is within a range of from 0.2 to 0.03.

* * * * *